United States Patent
Hess

(10) Patent No.: US 8,142,479 B2
(45) Date of Patent: Mar. 27, 2012

(54) INTERSPINOUS PROCESS IMPLANTS HAVING DEPLOYABLE ENGAGEMENT ARMS

(75) Inventor: Harold Hess, Leawood, KS (US)

(73) Assignee: Spinal Simplicity LLC, Overland Park, KS (US)

( * ) Notice: Subject to any disclaimer, the term of this patent is extended or adjusted under 35 U.S.C. 154(b) by 253 days.

(21) Appl. No.: 12/538,068

(22) Filed: Aug. 7, 2009

(65) Prior Publication Data

US 2009/0292316 A1 Nov. 26, 2009

Related U.S. Application Data

(63) Continuation-in-part of application No. 12/011,905, filed on Jan. 30, 2008, now Pat. No. 8,075,593.

(60) Provisional application No. 61/207,339, filed on Feb. 11, 2009, provisional application No. 61/007,916, filed on May 1, 2007, provisional application No. 60/959,799, filed on Jul. 16, 2007, provisional application No. 60/961,780, filed on Jul. 24, 2007, provisional application No. 61/000,831, filed on Oct. 29, 2007, provisional application No. 61/001,430, filed on Nov. 1, 2007.

(51) Int. Cl.
*A61B 17/70* (2006.01)
(52) U.S. Cl. .................. 606/248; 623/17.11; 623/17.16
(58) Field of Classification Search .................. 606/66, 606/68, 326, 60, 246–279, 63, 310, 323, 606/327; 623/17.11–17.16; 411/24–25, 411/32, 340
See application file for complete search history.

(56) References Cited

U.S. PATENT DOCUMENTS

| | | | |
|---|---|---|---|
| 4,116,104 A * | 9/1978 | Kennedy | 411/427 |
| 4,599,086 A | 7/1986 | Doty | |
| 4,721,103 A * | 1/1988 | Freedland | 606/319 |
| 4,998,936 A | 3/1991 | Mehdian | |
| 5,098,433 A * | 3/1992 | Freedland | 606/63 |

(Continued)

FOREIGN PATENT DOCUMENTS

GB 2 436 292 A 9/2007

(Continued)

OTHER PUBLICATIONS

International Search Report in PCT/US08/01231 dated Aug. 29, 2008.

(Continued)

*Primary Examiner* — Eduardo C Robert
*Assistant Examiner* — Michelle C Eckman
(74) *Attorney, Agent, or Firm* — Edwards Wildman Palmer LLP; Scott D. Wofsy; George N. Chacles

(57) ABSTRACT

Spinal implants include an elongated body portion dimensioned and configured for percutaneous introduction into a target interspinous process space, at which interspinous distraction and/or spinal fusion are desired. The body portion can include a threaded outer surface, or alternatively a smooth surface. The body portion can include one or more interior cavities, and can include deployable engagement members adapted and configured to move in tandem between a stowed position retracted within the interior cavity of the body portion and a deployed position extended from the interior cavity of the body for engaging adjacent spinous processes. An internal drive assembly for selectively moving the engagement members from the stowed position to the deployed position can be provided, as can a elements for locking the engagement members in a deployed position.

18 Claims, 10 Drawing Sheets

U.S. PATENT DOCUMENTS

| | | |
|---|---|---|
| 5,514,180 A | 5/1996 | Heggeness et al. |
| 5,645,599 A | 7/1997 | Samani |
| 5,653,761 A | 8/1997 | Pisharodi |
| 5,836,948 A | 11/1998 | Zucherman et al. |
| 5,849,004 A * | 12/1998 | Bramlet ................... 606/232 |
| 5,860,977 A | 1/1999 | Zucherman et al. |
| 5,876,404 A | 3/1999 | Zucherman et al. |
| 5,876,457 A | 3/1999 | Picha et al. |
| 5,904,686 A | 5/1999 | Zucherman et al. |
| 5,968,098 A | 10/1999 | Winslow |
| 6,017,342 A | 1/2000 | Rinner |
| 6,045,552 A | 4/2000 | Zucherman et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,093,207 A | 7/2000 | Pisharodi |
| 6,149,652 A | 11/2000 | Zucherman et al. |
| 6,152,926 A | 11/2000 | Zucherman et al. |
| 6,156,038 A | 12/2000 | Zucherman et al. |
| 6,174,334 B1 | 1/2001 | Suddaby |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,245,108 B1 | 6/2001 | Biscup |
| 6,264,677 B1 | 7/2001 | Simon et al. |
| 6,280,444 B1 | 8/2001 | Zucherman et al. |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,419,676 B1 | 7/2002 | Zucherman et al. |
| 6,419,677 B2 | 7/2002 | Zucherman et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,610,092 B2 | 8/2003 | Ralph et al. |
| 6,626,944 B1 | 9/2003 | Taylor |
| 6,652,527 B2 | 11/2003 | Zucherman et al. |
| 6,652,534 B2 | 11/2003 | Zucherman et al. |
| 6,682,564 B1 | 1/2004 | Duarte |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,709,435 B2 | 3/2004 | Lin |
| 6,712,819 B2 | 3/2004 | Zucherman et al. |
| 6,733,534 B2 | 5/2004 | Sherman |
| 6,743,256 B2 | 6/2004 | Mason |
| 6,746,485 B1 | 6/2004 | Zucherman et al. |
| 6,761,720 B1 | 7/2004 | Senegas |
| 6,770,096 B2 * | 8/2004 | Bolger et al. .............. 623/17.16 |
| 6,783,546 B2 | 8/2004 | Zucherman et al. |
| 6,796,983 B1 | 9/2004 | Zucherman et al. |
| 6,849,093 B2 | 2/2005 | Michelson |
| 6,860,977 B2 | 3/2005 | Heinz et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 7,029,473 B2 | 4/2006 | Zucherman et al. |
| 7,041,135 B2 | 5/2006 | Michelson |
| 7,083,649 B2 | 8/2006 | Zucherman et al. |
| 7,101,375 B2 | 9/2006 | Zucherman et al. |
| 7,125,425 B2 | 10/2006 | Foley et al. |
| 7,189,234 B2 | 3/2007 | Zucherman et al. |
| 7,192,446 B2 | 3/2007 | Shapiro et al. |
| 7,201,751 B2 | 4/2007 | Zucherman et al. |
| 7,217,291 B2 | 5/2007 | Zucherman et al. |
| 7,232,464 B2 | 6/2007 | Mathieu et al. |
| 7,238,186 B2 | 7/2007 | Zdeblick et al. |
| 7,238,204 B2 | 7/2007 | Le Couedic et al. |
| 7,306,628 B2 | 12/2007 | Zucherman et al. |
| 7,320,707 B2 | 1/2008 | Zucherman et al. |
| 7,326,248 B2 | 2/2008 | Michelson |
| 7,410,501 B2 | 8/2008 | Michelson |
| 7,423,268 B2 | 9/2008 | Ren |
| 7,445,636 B2 | 11/2008 | Michelson |
| 7,445,637 B2 | 11/2008 | Taylor |
| 7,465,317 B2 | 12/2008 | Malberg et al. |
| 7,465,318 B2 | 12/2008 | Sennett et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,497,859 B2 | 3/2009 | Zucherman et al. |
| 7,503,935 B2 | 3/2009 | Zucherman et al. |
| 7,510,567 B2 | 3/2009 | Zucherman et al. |
| 7,520,899 B2 | 4/2009 | Zucherman et al. |
| 7,662,187 B2 | 2/2010 | Zucherman et al. |
| 7,918,875 B2 | 4/2011 | Lins et al. |
| 8,007,517 B2 | 8/2011 | Lins et al. |
| 2004/0024463 A1 | 2/2004 | Thomas et al. |
| 2005/0165398 A1 * | 7/2005 | Reiley ............................ 606/61 |
| 2005/0196420 A1 | 9/2005 | Zucherman et al. |
| 2005/0245929 A1 | 11/2005 | Winslow et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0084985 A1 | 4/2006 | Kim |
| 2006/0089718 A1 | 4/2006 | Zucherman et al. |
| 2006/0184247 A1 | 8/2006 | Edidin et al. |
| 2006/0195102 A1 | 8/2006 | Malandain |
| 2006/0247634 A1 | 11/2006 | Warner et al. |
| 2006/0247783 A1 * | 11/2006 | McKay ..................... 623/17.16 |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271049 A1 | 11/2006 | Zucherman et al. |
| 2006/0271194 A1 | 11/2006 | Zucherman et al. |
| 2007/0010813 A1 * | 1/2007 | Zucherman et al. ........... 606/61 |
| 2007/0032790 A1 | 2/2007 | Aschmann et al. |
| 2007/0055291 A1 | 3/2007 | Birkmeyer et al. |
| 2007/0093830 A1 | 4/2007 | Zucherman et al. |
| 2007/0185490 A1 | 8/2007 | Implicito |
| 2007/0225706 A1 * | 9/2007 | Clark et al. ..................... 606/61 |
| 2008/0183211 A1 | 7/2008 | Lamborne et al. |
| 2008/0243250 A1 * | 10/2008 | Seifert et al. ............... 623/17.16 |
| 2008/0281359 A1 | 11/2008 | Abdou |
| 2008/0312741 A1 * | 12/2008 | Lee et al. ................... 623/17.11 |
| 2009/0054988 A1 | 2/2009 | Hess |
| 2009/0164020 A1 * | 6/2009 | Janowski et al. .......... 623/17.16 |
| 2009/0198338 A1 * | 8/2009 | Phan ......................... 623/17.16 |
| 2009/0265006 A1 * | 10/2009 | Seifert et al. .............. 623/17.16 |
| 2009/0281626 A1 | 11/2009 | Farr |
| 2009/0292316 A1 | 11/2009 | Hess |
| 2010/0057130 A1 * | 3/2010 | Yue .............................. 606/249 |
| 2010/0106191 A1 | 4/2010 | Yue et al. |
| 2010/0114166 A1 * | 5/2010 | Kohm et al. ................. 606/247 |
| 2010/0152775 A1 | 6/2010 | Seifert et al. |
| 2010/0318127 A1 * | 12/2010 | Phan et al. ................... 606/249 |

FOREIGN PATENT DOCUMENTS

| | | |
|---|---|---|
| WO | WO-2008/088613 A2 | 7/2008 |
| WO | WO 2008/118907 A2 | 10/2008 |
| WO | WO-2009/132059 A1 | 10/2009 |

OTHER PUBLICATIONS

Written Opinion in PCT/US08/01231 dated Aug. 29, 2008.
Medtronic: CD Horizon Spire (Trademark), Stabilization System, Information Brochure, James Robinson, MD, 2006.
St. Francis Medical Technologies, Inc., "A Patient's Guide to Lumbar Spinal Stenosis," & "X STOP (Trademark)—Interspinous Process Decompression," Information Guide, Sep. 16, 2005.
International Search Report in PCT/US09/006742 dated Apr. 16, 2010.
Written Opinion in PCT/US09/006742 dated Apr. 16, 2010.
International Search Report dated May 7, 2010.
US 7,520,878, 04/2009, Michelson (withdrawn)

* cited by examiner

INTERSPINOUS PROCESS IMPLANTS HAVING DEPLOYABLE ENGAGEMENT ARMS

CROSS-REFERENCE TO RELATED APPLICATIONS

This application is a continuation-in-part application of, and claims the benefit of priority to U.S. patent application Ser. No. 12/011,905, filed Jan. 30, 2008, which in-turn claims priority to U.S. Patent Application Ser. No. 61/001,430, filed Nov. 1, 2007, U.S. Patent Application Ser. No. 61/000,831, filed Oct. 29, 2007, U.S. Patent Application Ser. No. 60/961,780, filed Jul. 24, 2007, U.S. Patent Application Ser. No. 60/959,799, filed Jul. 16, 2007, and U.S. Patent Application Ser. No. 61/007,916, filed May 1, 2007. This application also claims the benefit of priority to U.S. Patent Application Ser. No. 61/207,339, filed Feb. 11, 2009. Each of the aforementioned patent applications is incorporated herein by reference in its entirety.

BACKGROUND OF THE INVENTION

1. Field of the Invention

The subject invention is directed to spinal implants, and more particularly, to an interspinous process implant with a threaded body and deployable engagement arms for percutaneous placement in the interspinous process space to treat lumbar spinal stenosis.

2. Description of Related Art

The spine consists of a column of twenty-four vertebrae that extend from the skull to the hips. Discs of soft tissue are disposed between adjacent vertebrae. The vertebrae provide support for the head and body, while the discs act as cushions. In addition, the spine encloses and protects the spinal cord, which is surrounded by a bony channel called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are number of non-surgical treatments of stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord or nerves between the spinous processes that protrude from the vertebrae in the lower back. A well-known implant used for performing IPD surgery is the X-STOP® device, which was first introduced by St. Francis Medical Technologies, Inc. of Alameda Calif. However, implantation of the X-STOP® device still requires an incision to access the spinal column to deploy the X-STOP® device.

It would be advantageous to provide an implant for performing IPD procedures that could be percutaneously inserted into the interspinous process space and effectively treat lumbar spinal stenosis.

SUMMARY OF THE INVENTION

The subject invention is directed to a new and useful spinal implant that includes, in one aspect, a spinal implant comprising: an elongated dimensioned and configured for percutaneous introduction into the interspinous process space. The body portion can be fully or partially threaded, or alternatively have a smooth surface.

The body portion can include an interior cavity, and further comprises deployable engagement members adapted and configured to move in tandem between a stowed position retracted within the interior cavity of the body portion and a deployed position extended from the interior cavity of the body for engaging the spinous process.

A drive assembly can be provided, extending into the interior cavity of the threaded body portion for selectively moving the engagement members in tandem from the stowed position to the deployed position. Means for selectively locking the engagement members in the deployed position, operatively associated with the drive assembly, can be provided. The drive assembly can include a main drive shaft that extends into the interior cavity of the body portion along the longitudinal axis of the body portion. The drive shaft can include a transmission end having a plurality of beveled gear teeth for operatively meshing with the beveled gear teeth on the central hubs of each engagement member to facilitate the transmission of torque therebetween.

Two engagement members can be provided for engaging the spinous process, wherein each engagement member includes a pair of curved engagement arms extending radially outwardly from a central hub. The central hub of each engagement member can include a plurality of beveled gear teeth and be mounted for rotation about a common shaft extending transverse to the longitudinal axis of the body portion. Each engagement arm can include a distal claw portion having a plurality of dissimilar teeth for engaging the spinous process.

In accordance with the invention, a threaded body portion can include an outer profile, tapering axially inwardly in a distal nose portion thereof, configured to gradually distract adjacent spinous processes during insertion, or advancement, of the implant into the interspinous process space. Threads can be provided on the body portion, and can extend at least partially over the nose portion thereof. The distal nose portion can taper axially inwardly with respect to a central region of the body, by an angle of between about 5 degrees and 65 degrees, with respect to a longitudinal axis thereof. In accordance with one aspect of the invention, this angle can be between about 15 and 45 degrees. In accordance with another aspect, this angle can be between about 25 and 35 degrees. In accordance with another aspect, this angle can be about 30 degrees.

An interior core portion adapted and configured for rigidifying the spinal implant can be provided and arranged within the body portion of the subject implants. Such core portions can include an integral tip portion, arranged at the distal end of the implant. If desired, a separately formed tip portion can be provided and arranged at the distal end of the implant, with or without such a core portion.

In accordance with the invention, the body portion and the tip portion can be formed of dissimilar materials.

The tip portion can include an axially inward taper, and can be provided with or without threads on the outer surface thereof, depending on the precise implementation.

The body portion can include a separately formed proximal portion, formed of a material dissimilar from a material from which a central portion of the body portion is formed. The proximal portion can be formed of a metal material, and the central portion of the body portion can be formed of a polymeric material, for example.

At least one detent can be provided on the implant for aligning the implant with an insertion device therefor.

In accordance with another aspect of the invention, a spinal implant includes an elongated body portion dimensioned and configured for percutaneous introduction into the interspinous process space and having an interior cavity, deployable engagement members adapted and configured to move in tandem between a stowed position retracted within the interior cavity of the body portion and a deployed position extended from the interior cavity of the body for engaging the spinous process, and a rotatable drive shaft extending into the interior cavity of the threaded body portion along the longitudinal axis thereof for selectively moving the engagement members in tandem from the stowed position to the deployed position.

A locking cap can be provided, operatively associated with the rotatable drive shaft and the body portion for selectively locking the engagement members in the deployed position.

Two engagement members can be provided for engaging the spinous process, wherein each engagement member includes a pair of curved engagement arms extending radially outwardly from a central hub. The central hub of each engagement member can include a plurality of beveled gear teeth and is mounted for rotation about a common shaft extending transverse to the longitudinal axis of the body portion.

A drive shaft can be provided, including a transmission end having a plurality of beveled gear teeth for operatively meshing with the beveled gear teeth on the central hubs of each engagement member to facilitate the transmission of torque therebetween. Each engagement arm can include a distal claw portion having a plurality of dissimilar teeth for engaging the spinous process.

In accordance with still another aspect of the invention, a method of lateral insertion of a spinal implant into an interspinous process space is provided, comprising the steps of forming an incision in a patient's skin, lateral from a target interspinous process space, in which the implant is to be placed, inserting a stylet through the incision, laterally to the target interspinous process space, using an internal imaging technique, to form an entry path, inserting one or more dilators, sequentially, along the entry path to dilate soft tissues between the incision and the target interspinous process space, inserting a sleeve through the entry path, selecting an implant having a size appropriate for a desired amount of interspinous distraction, inserting the implant, held by an insertion device, through the sleeve, up to the target interspinous process space, and advancing the implant into the interspinous process space.

Methods in accordance with the invention can further include the following steps, for example. Such methods can further include a step of aligning the implant with spinous processes of the patient following the advancing step.

The advancing step can include rotating the implant along a longitudinal axis thereof, to effect axial advancement of the implant by way of threads formed on an outer surface thereof.

Such methods can further include a step of deploying engagement members, when the implant includes a plurality of engagement members for engaging adjacent spinous processes to the target interspinous process space.

Fluoroscopy can be used as an internal imaging technique during insertion of the stylet and optionally throughout the procedure, such as during insertion of the implant itself.

A tap can be inserted into the target interspinous process space, and used to form threads on surfaces of adjacent spinous processes, prior to insertion of a threaded implant, for engagement with threads of the implant.

Methods of the invention can further include the step of filling one or more cavities in the implant with an osteogenesis promoting substance. The osteogenesis promoting substance can be, for example, demineralized bone gel.

It is to be understood that each feature of the disclosed implants and related methods may be interchanged and coupled freely with the various other features to utilize any combination thereof. These and other features of the interspinous implant and percutaneous placement method of the subject invention will become more readily apparent to those skilled in the art from the following detailed description of the preferred embodiment taken in conjunction with the drawings.

BRIEF DESCRIPTION OF THE DRAWINGS

So that those skilled in the art to which the subject invention appertains will readily understand how to make and use the interspinous implant of the subject invention without undue experimentation, preferred embodiments thereof will be described in detail herein below with reference to certain figures, wherein.

DETAILED DESCRIPTION

Figure 1:
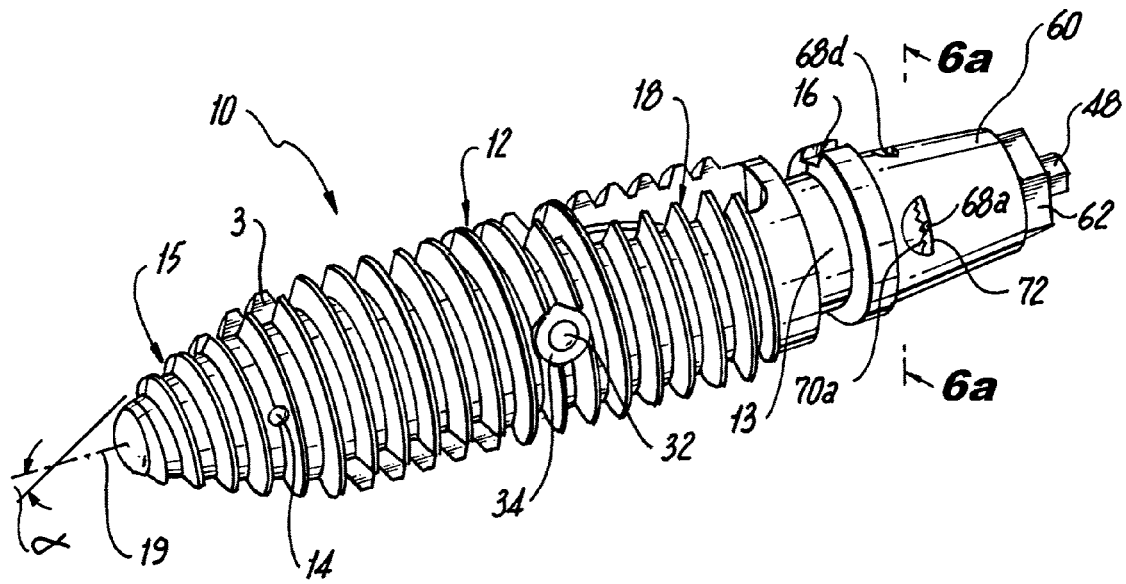
FIG. 1 is a perspective view of an interspinous implant constructed in accordance with a preferred embodiment of the subject invention, which includes a threaded body portion (shown in phantom view) dimensioned and configured for percutaneous introduction into the interspinous process space of a patient and a set of engagement arms for selectively engaging the spinous process, the engagement arms being disposed in a stowed position within the interior cavity of the threaded body portion.

Referring now FIG. 1, there is illustrated one exemplary embodiment of an interspinous implant constructed in accordance with a preferred embodiment of the subject invention and designated generally by reference numeral 10. Implant 10 is particularly well adapted for use in performing minimally invasive surgical procedures for treating spinal stenosis, including, for example, interspinous process decompression (IPD).

It is envisioned however, that the implant 10 of the subject invention can be used in other spinal procedures as well, including, but not limited to as an adjunct to spinal fusion procedures, or as a spinal stabilization device. Those skilled in the art will readily appreciate from the following description that the interspinous process implant of the subject invention is well adapted for percutaneous insertion, and thus overcomes many of the deficiencies of prior art devices presently used in IPD procedures. That is, the implant 10 is dimensioned and configured for introduction and placement through a small skin incision rather than in an open surgical procedure involving a cut down of tissue.

Referring to FIGS. 1 through 5, the interspinous implant 10 of the subject invention includes a threaded body portion 12 having right and left body sections 12a, 12b. The body sections 12a, 12b are held together in part by a securement pin 14 located adjacent the tapered nose cone 15 of the implant body 12.

The two body sections 12a, 12b are preferably formed from a biocompatible polymeric material that has a modulus of elasticity that is substantially similar to that of bone, for example, polyaryletheretherketone thermoplastic (PEEK) or a similar material. However, the body sections could also be made from machined bone, from a biocompatible metal such as, for example, a titanium alloy or stainless steel, a ceramic, a composite or a like material or combination thereof.

The body portion 12 is dimensioned and configured for threaded placement between the spinous processes of symptomatic disc levels. In this regard, it is envisioned that the outer diameter of the implant 10 can range from about 8.0 mm to about 16.0 mm, with the thread depth being about 1.0 mm. The threads on the body portion 12 of the implant 10 can be configured so that the implant is self-tapping to ease insertion of the implant into the interspinous process space, as described below in connection with FIGS. 12 and 13.

In the embodiment illustrated in FIGS. 1-7, an optional detent 3, in this embodiment composed of detents 3a and 3b, respectively formed in the two body sections 12a and 12b, is provided for engaging an insertion device in a bilateral insertion technique, in which insertion devices are attached to both the proximal and distal ends of the implant, engaging the detent 3. Such a technique is described in U.S. Patent Publication No. 2009/0054988, which is incorporated herein by reference in its entirety.

It is envisioned that implant 10 can have a variety of thread forms, such as, for example, cutting threads or box threads. It is also envisioned that the body portion of the implant can be provided without threads, while remaining well within the scope of the subject disclosure, and as discussed in more detail hereinbelow, in connection with FIGS. 16 and 17.

In addition to facilitating advancement of the implant 10 into a target interspinous process space through axial rotation, thereof, the threads on implant 10 also assist in spinal stabilization by engaging corresponding threads that are formed prior to or during insertion, in the adjacent spinous processes, as will be described in more detail hereinbelow.

Furthermore, as illustrated, the distal end portion of the implant 10 includes a tapered nose portion 15, and therefore gradually dilates the interspinous process space during insertion. Accordingly, a separate spreader is not required for dilating the interspinous process space prior to insertion of the implant 10. The distal nose portion 15, as illustrated, tapers axially inwardly with respect to a central region of the body, by an angle $\alpha$ (alpha) of between about 5 degrees and 65 degrees, with respect to a longitudinal axis 19 thereof. In accordance with one aspect of the invention, this angle $\alpha$ (alpha) can be between about 15 and 45 degrees. In accordance with another aspect, this angle $\alpha$ (alpha) can be between about 25 and 35 degrees. In accordance with another aspect, this angle can be about 30 degrees. It is to be understood, however, that the angle $\alpha$ (alpha) should not be limited to the aforementioned ranges. Further, it is to be understood that these ranges can apply to other embodiments of the invention.

Moreover, being provided with such threads, the implant 10 can be employed as a threaded fusion cage for the interspinous process space, as will be appreciated by those skilled in the art. To facilitate implementation as a fusion cage, the body portion 12 can be provided with several apertures or cutouts which allow for the insertion of demineralized bone or another type of fusion adjunct material, which apertures also promote bone ingrowth, as will be discussed further below.

Figure 2:
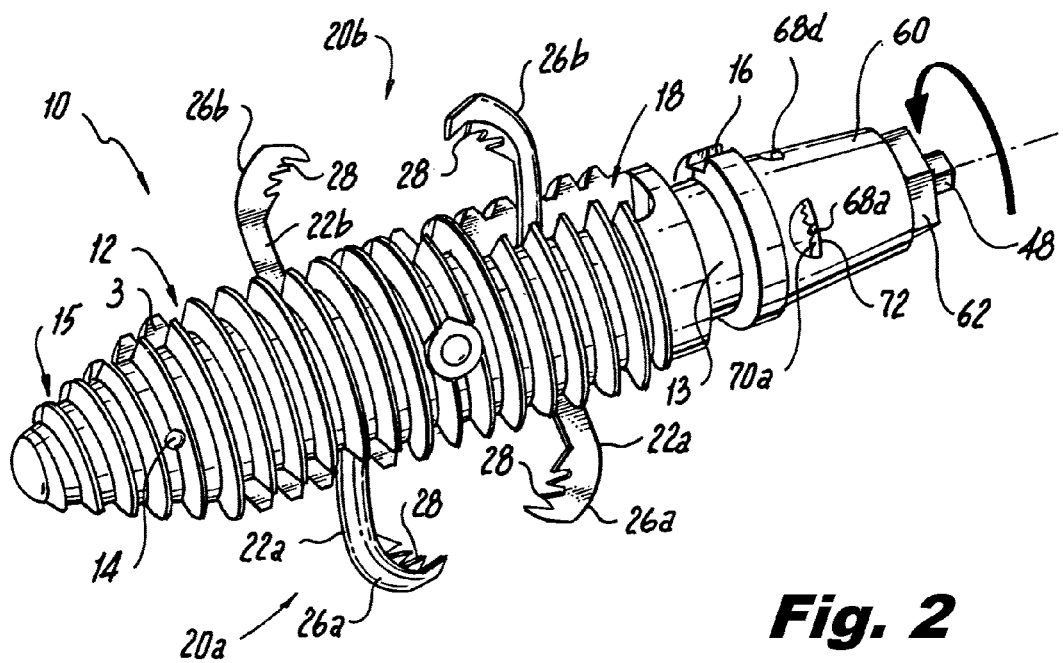
FIG. 2 is a perspective view of the interspinous implant of FIG. 1, with the engagement arms disposed in a deployed position extending from the interior cavity of the threaded body portion.

The body portion 12 of implant 10 defines an interior cavity 18 or chamber which houses two deployable engagement members 20a, 20b formed from titanium, stainless steel, ceramic, composite, or a similar high-strength, light-weight biocompatible metal. The engagement members 20a, 20b are adapted and configured to move in tandem between a stowed position retracted within the interior cavity 18 of the body portion 12, as shown in FIG. 1, and a deployed position extended from the interior cavity 18 of the body portion 12, as shown in FIG. 2, for engaging the spinous processes. Advantageously, once the engagement members 20a, 20b are deployed to engage the spinous processes, migration of the implant 10 is inhibited, in addition to lateral migration resistance provided by the threads alone.

Figure 3:
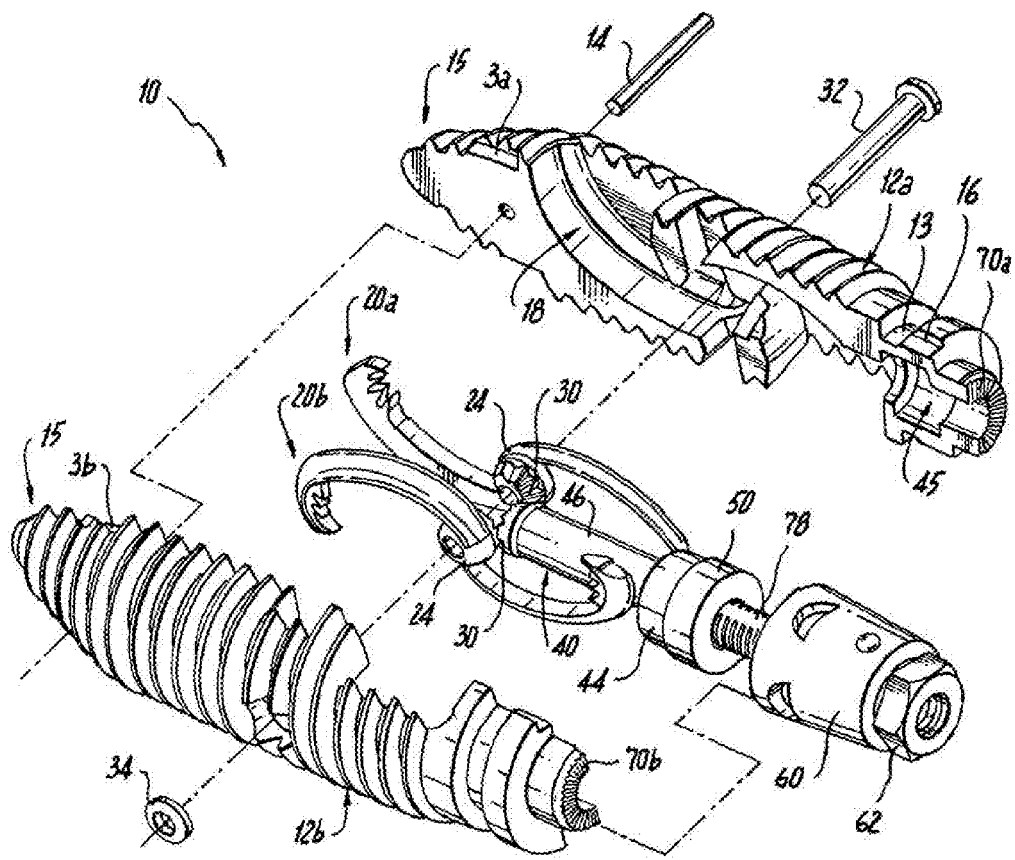
FIGS. 3, 4 and 5 are exploded perspective views of the interspinous implant of the FIG. 1, with parts separated for ease of illustration.
Figure 4:
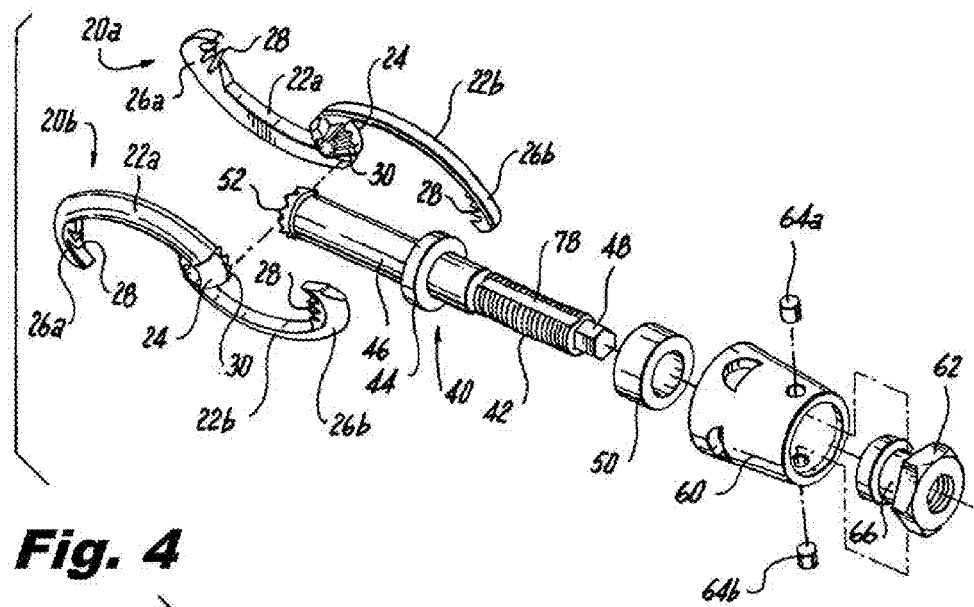
Figure 5:
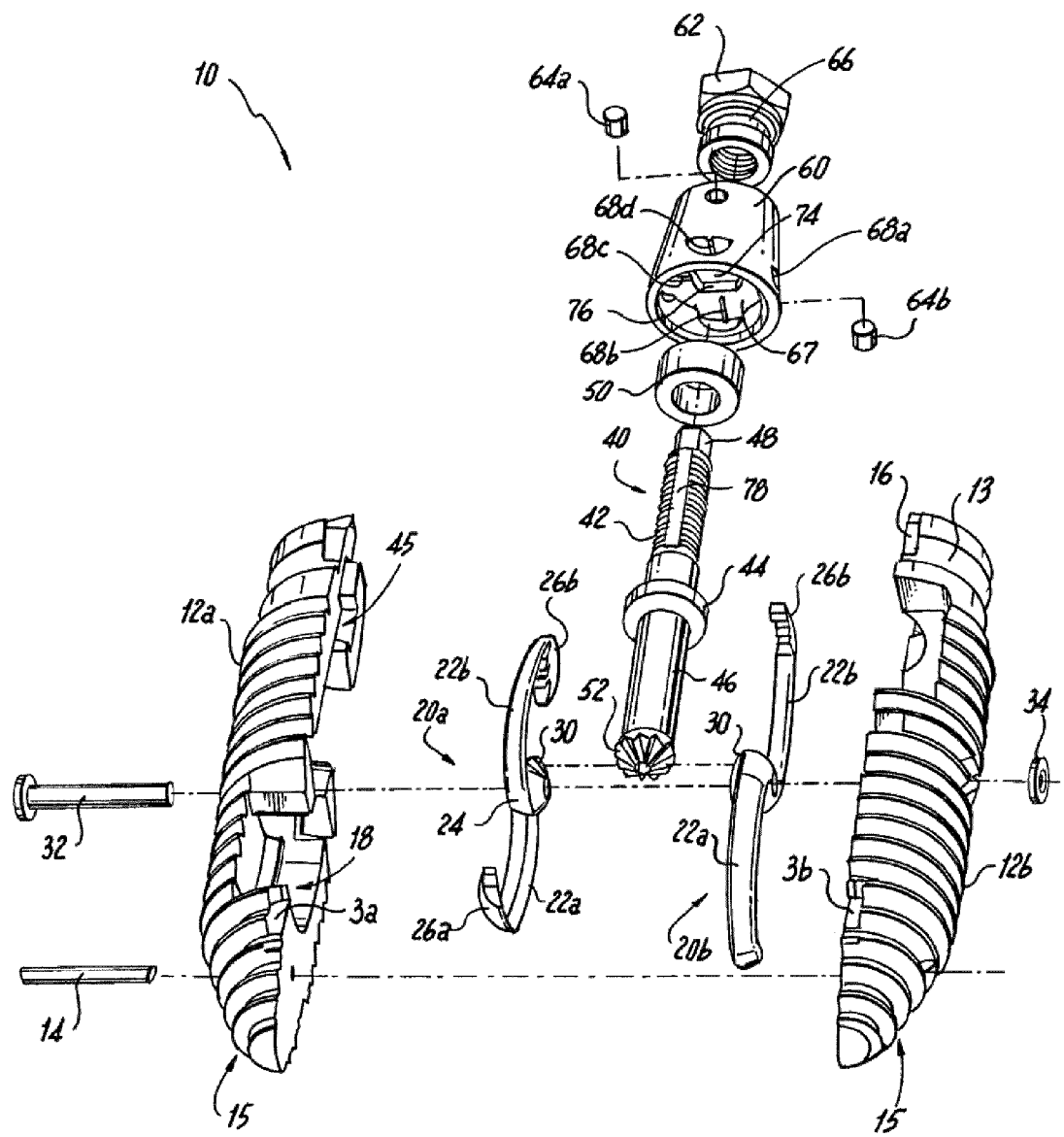

As illustrated, and best seen in FIGS. 3-5, each engagement member 20a, 20b includes a pair of curved engagement arms 22a, 22b that extend radially outwardly in an arcuate manner from a central hub 24. In the illustrated embodiments, each engagement arm 22a, 22b includes a distal claw portion 26a, 26b. The claw portions 26a, 26b of the engagement arms 22a, 22b are preferably each provided with a plurality of sharpened teeth 28 for engaging and puncturing the bone of the adjacent spinous processes, to effect stabilization of the implant 10. The teeth 28 on each claw portion 26a, 26b are preferably, but not necessarily, dissimilar in size and orientation, to better engage an individual's particular anatomy, which may vary between patients in both size and shape.

The central hub 24 of each engagement member 20a, 20b includes a plurality of beveled gear teeth 30 and is mounted for rotation about a spindle shaft 32 extending transverse to the longitudinal axis of the body portion 12. The spindle shaft 32 is secured in place within the body portion 12 of implant 10 by a retaining ring 34, such as a nut, circlip, snap or press-fit ring or by other mechanical fastener known in the art. In accordance with a preferred aspect, the ring 34, or alternatively a cap or termination having another suitable configuration is welded to the spindle shaft 32. In a preferred embodiment, this welding is accomplished by laser welding. In the embodiment of FIGS. 1-5, the spindle shaft 32 and retaining ring 34 also serve to hold body section 12a, 12b together, in conjunction with a more proximally arranged securement pin 14.

The interspinous implant 10 further includes an actuation assembly defined in part by an elongated drive shaft 40 that extends into the interior cavity 18 of the body portion 12 along the longitudinal axis thereof. The drive shaft 40 includes a proximal threaded section 42, a medial support flange 44 and a distal drive section 46. The proximal threaded section 42 includes a hexagonal shaped end-fitting 48 for cooperating with an insertion device (not shown in FIGS. 1-5) having a receptacle for receiving at least the end-fitting 48 of the shaft 40. The insertion device is used to axially rotate or otherwise actuate the drive shaft 40 to facilitate selective deployment of the engagement members 20a, 20b.

The medial support flange 44 of drive shaft 40 is accommodated within a journal chamber 45 formed within the proximal end portion of the interior cavity 18 of body portion 12, together with an annular bushing 50 that supports the axial rotation of drive shaft 40. The distal drive section 46 of drive shaft 40 includes a distal bevel gear 52 adapted and configured to operatively mesh with and transmit torque to the beveled gear teeth 30 on the central hub portion 24 of each engagement member 20a, 20b to selectively rotate the engagement arms 22a, 22b of the two engagement members 20a, 20b, in tandem, into a deployed position, as illustrated, for example in FIGS. 2 and 11.

A locking cap 60 is operatively associated with the threaded proximal section 42 of drive shaft 40. Locking cap 60 serves two functions. First, locking cap 60 functions to hold body sections 12a, 12b together, in conjunction with securement pin 14 and spindle shaft 32. In addition, locking cap 60 functions to selectively lock the paired engagement arms 22a, 22b of engagement members 20a, 20b in a deployed position. More particularly, the locking cap 60 is cooperatively associated with a threaded lock nut 62 by way of a pair of opposed set pins 64a, 64b which are captured within an annular channel 66 formed in lock nut 62. Lock nut 62 is threadedly associated with the threaded proximal section 42 of drive shaft 40.

In addition, locking cap 60 includes an interior planar surface 67, as best seen in FIG. 5, having a set of four locking ribs 68a-68d provided thereon. These ribs 68a-68d are dimensioned and configured to lockingly rotationally engage with a toothed annular surface 70a, 70b (see FIG. 3) provided on the proximal end of body portions 12a, 12b. The locking interaction of the ribs 68a-68d and toothed annular surface 70a, 70b, best seen in FIGS. 1 and 2 through the semi-circular port 72 formed in the side wall of locking cap 60. The ports 72, which can be provided in one or more circumferentially opposed pairs, can facilitate machining of internal features of the locking cap 60.

In use, once the engagement arms 22a, 22b of each engagement member 20a, 20b have been deployed by axially rotating drive shaft 40, the locking cap 60 is moved axially into a locking position by rotation of the threaded lock nut 62, until such time as the locking ribs 68a-68d of the locking cap 60 engage the toothed annular surface 70a, 70b on the proximal end of body portions 12a, 12b. It should be noted that although the engagement arms 22a, 22b are deployed in tandem, as embodied, the invention is not limited to such configuration.

Figures 6, 7:
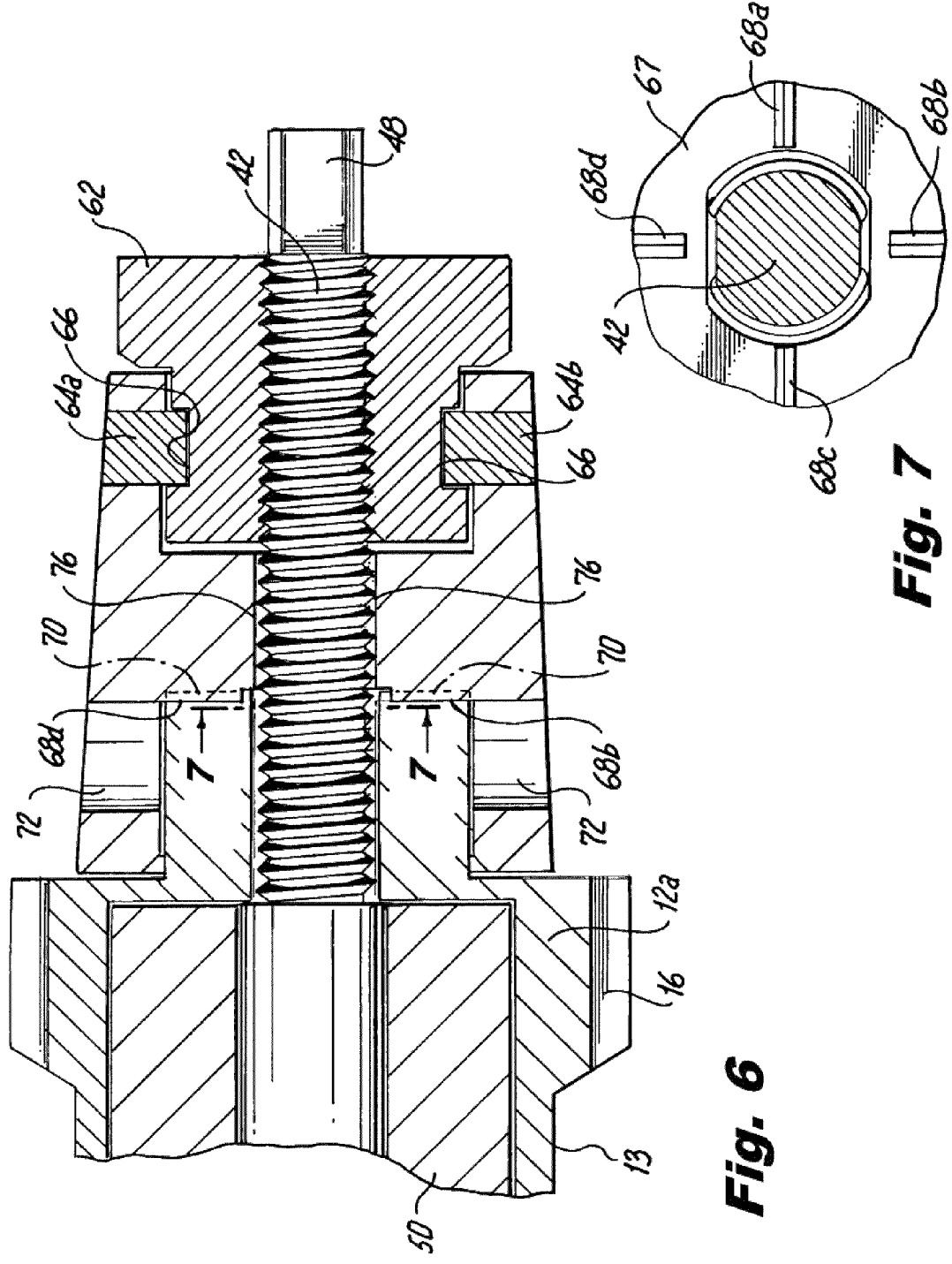
FIG. 6 is a detail cross-sectional view of a proximal end portion of the interspinous implant of the FIG. 1, taken along line 6-6 of FIG. 1.
FIG. 7 is a transverse cross-sectional view, as seen facing the proximal end of the interspinous implant of the FIG. 1, taken along line 7-7 of FIG. 6.

As best seen in FIGS. 5-7, there is an aperture 74 formed in the planar surface 67 of locking cap 60 that includes diametrically opposed flat surfaces 76 corresponding to diametrically opposed longitudinal lands 78 formed on the threaded portion 42 of the drive shaft 40. The interaction between the opposed surfaces 76 of aperture 74 and the opposed lands 78 of threaded portion 42 allow axial movement of locking cap 60, relative to the drive shaft 40, while preventing rotation of the locking cap 60 relative to drive shaft 40, as locking cap 60 is moved into a locking position through rotation of lock nut 62.

Further, one or more alignment and/or engagement features can be provided on the interspinous implant 10, for engaging an insertion device therefor. As illustrated in the embodiment of FIGS. 1-7, an annular recess 13, can be provided in the proximal region of the implant 10 for securing the implant to an insertion device, limiting unintentional relative axial motion. In conjunction with the annular recess 13, one or more axial, circumferentially outer grooves 16 can be provided for limiting unintentional relative rotational movement therebetween.

Figure 8:
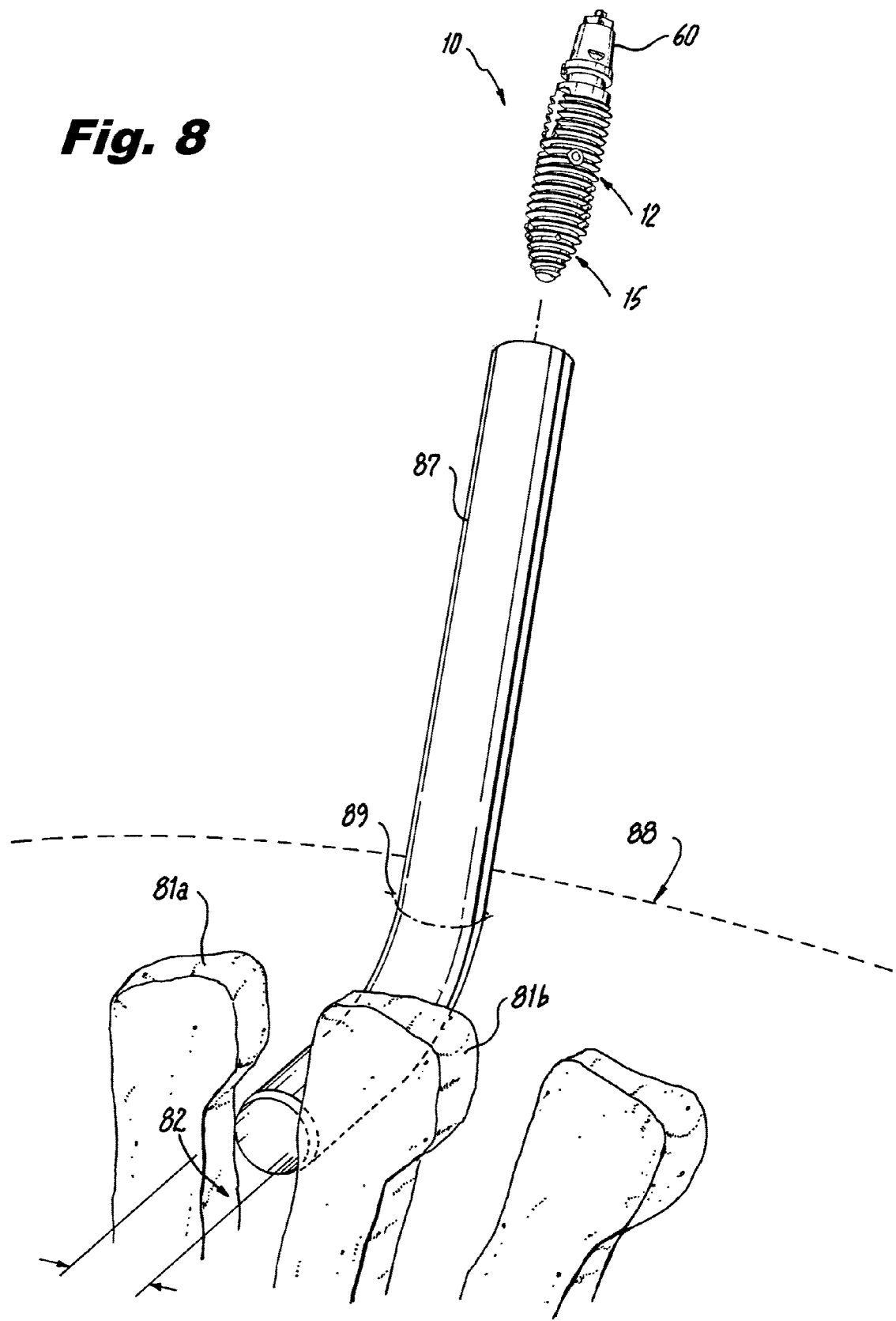
FIG. 8 is a representational view illustrating a dorsal insertion technique, illustrated with the interspinous implant of the FIG. 1, applicable to all embodiments of the invention.

FIGS. 8-11 illustrate example aspects of insertion of devices in accordance with the invention, and are described in connection with the interspinous implant of FIGS. 1-7. As seen in FIG. 8, a sleeve 87 is provided to facilitate insertion. The insertion methods can include use of a stylet, dilators, and the like to gain access and define a path for the sleeve 87, as will be described in more detail below. However, dorsal insertion can be accomplished as set forth in U.S. patent application Ser. No. 12/011,905, filed Jan. 30, 2008 (U.S. Pub. No. 2009/0054988), which is incorporated herein by reference in its entirety.

As illustrated, in FIG. 8, dorsal insertion of the subject implants, represented by implant 10, can be effected by forming an incision 89 through the skin 88 of a patient, at a level corresponding to a target interspinous process space 82, defined between adjacent vertebral processes 81a, 81b. With dorsal entry illustrated in FIG. 8, the path traversed by the implant 10, and therefore also by the sleeve 87 is curved to align the path and the implant 10 with the target interspinous process space 82.

Figure 9:
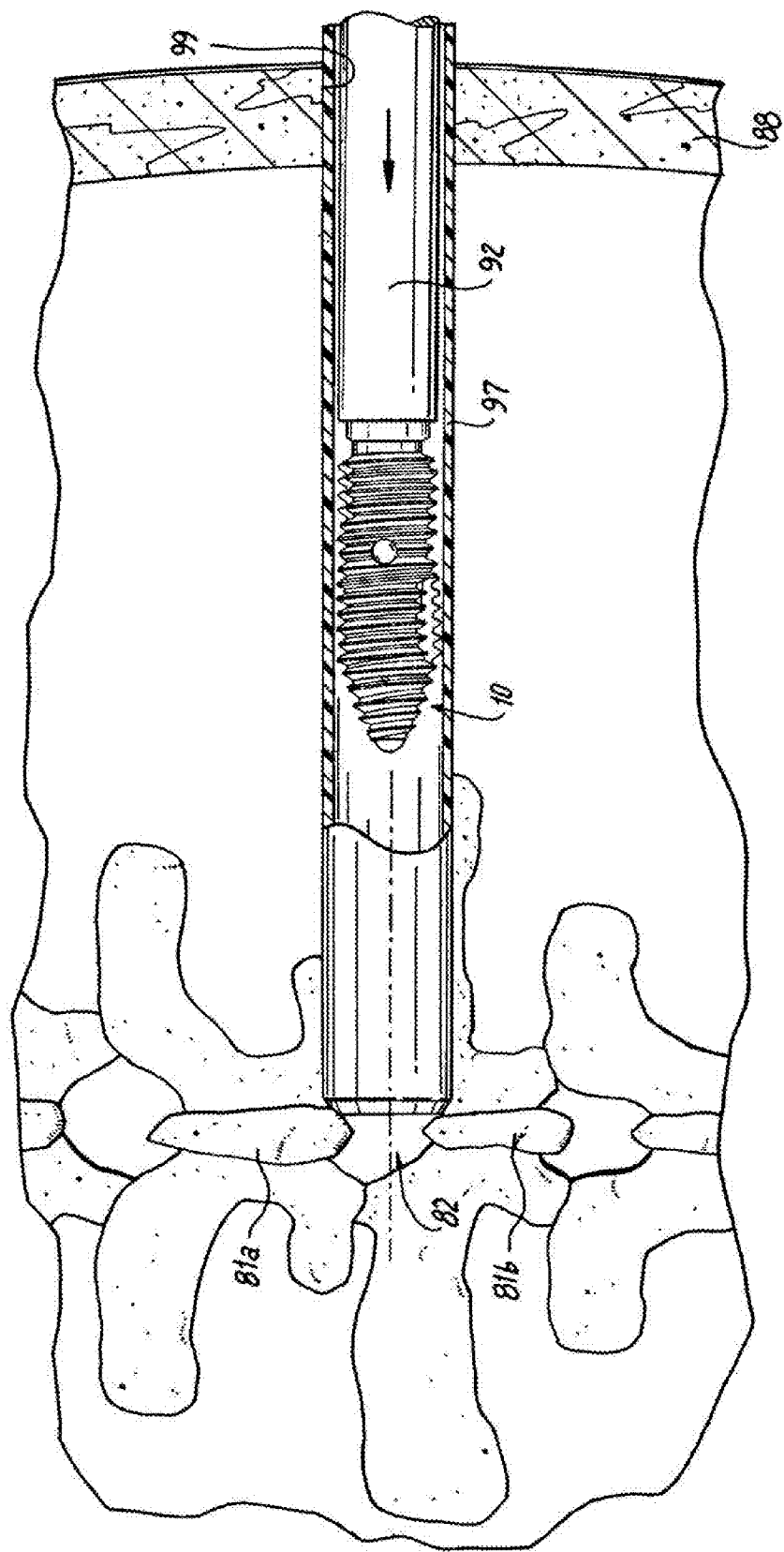
FIG. 9 is a representational view illustrating a lateral insertion technique, illustrated with the interspinous implant of the FIG. 1, applicable to all embodiments of the invention.
Figure 10:
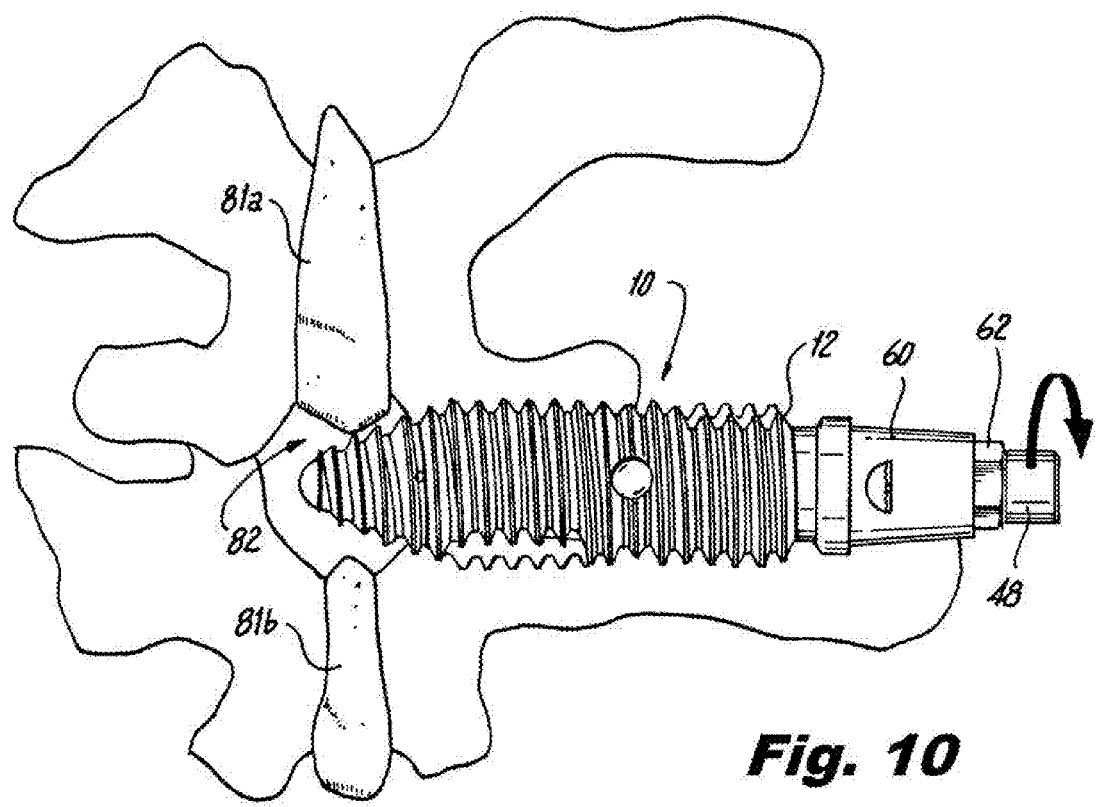
FIG. 10 is a rear (dorsal side) representational view, illustrating advancement of the interspinous implant of the FIG. 1, applicable to all embodiments of the invention.
Figure 11:
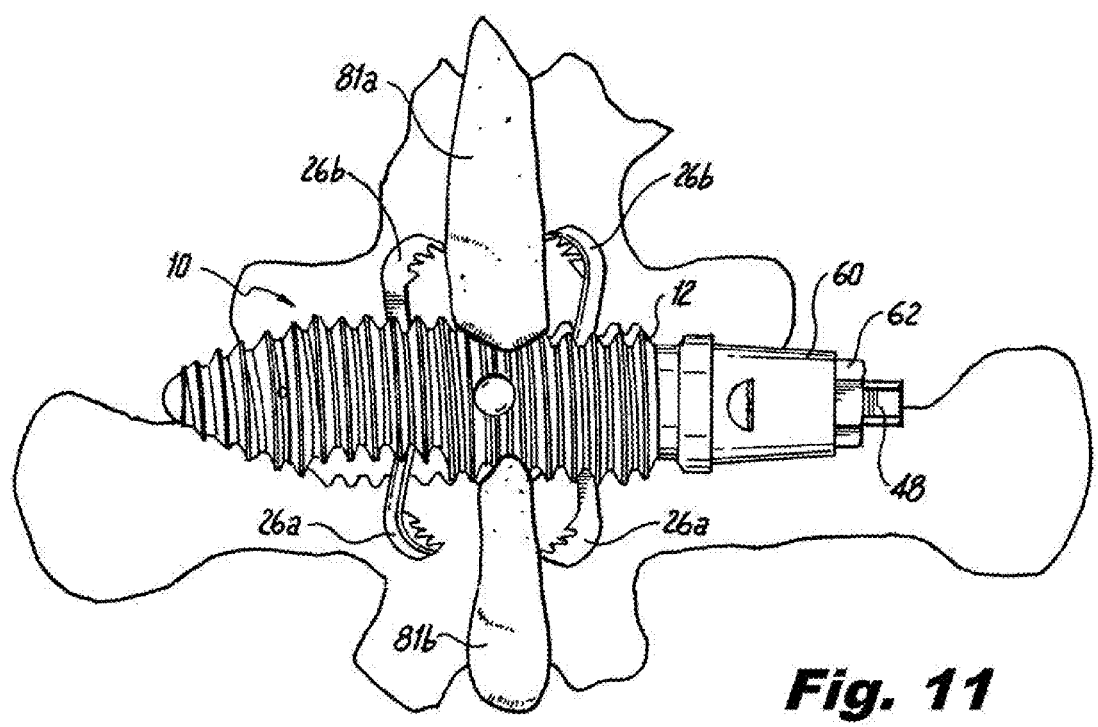
FIG. 11 is a rear (dorsal side) representational view, illustrating the interspinous implant of the FIG. 1, having engagement arms deployed, engaging adjacent spinous processes.

FIG. 9, in contrast, illustrates direct lateral insertion of the implant 10 into the target interspinous process space 82. In this arrangement, an incision 99 is formed in the skin 88 of a patient, and ultimately a sleeve 97 is advanced through the tissue to the target interspinous process space 82, through which the implant 10 is advanced, connected to the insertion device 92. As shown in FIGS. 10 and 11, which are illustrated for clarity without the sleeve 97, the insert 10 is axially rotated by way of the insertion device 92, thus threading the implant 10 into the target interspinous process space 82, distracting the adjacent spinous processes 81a, 81b, and advancing the implant into its final position, generally centered with respect to the spinous processes 81a, 81b. During the rotation of the implant 10, relative rotation and axial translation between the implant 10 and the insertion device 92 is preferably inhibited by the above-mentioned grooves 13, 16. When in position, the engagement arms 22a, 22b can be actuated into the deployed configuration shown in FIG. 11. Subsequently, the lock nut 62 can be tightened, advancing the locking cap 60 distally into engagement with the body 12, thus rotationally engaging the locking cap 60 with the body 12 by way of the toothed surface 70 and ribs 68a-68d, described hereinabove. Moreover, the lock nut 62 maintains frictional engagement with the locking cap 60, to axially and rotationally secure the lock nut 62 and locking cap 60. Subsequently, one or more osteogenesis promoting substances can be packed in and/or around the implant 10 to promote spinal fusion, if desired.

The set pins 64a and 64d, are provided in the illustrated embodiment for maintaining an axial connection (with respect to a central longitudinal axis of the implant), keeping the locking cap 60 and lock nut 62 together, while permitting axial rotation of the lock nut 62, with respect to the locking cap 60. Accordingly, tightening of the lock nut 62 causes rotational locking engagement between the body 12, locking cap 60 and the drive shaft 40, fixing the position of the engagement arms 22a, 22b. Similarly, loosening of the lock nut 62 pulls the locking cap 60 proximally by way of the set pins 64a and 64d, permitting unlocking and retraction of the engagement arms 22a, 22b to permit removal of the implant 10.

A separate tap can be used before the insertion of the implant, or the implant can be provided with features that provide self-tapping capability, as described herein.

As discussed above, methods of lateral insertion of the spinal implant 10 into a target interspinous process space 82 can include, following forming the incision 99, inserting a stylet (not illustrated) through the incision, laterally to the target interspinous process space 82, preferably using an internal imaging technique, such as fluoroscopy. Insertion of the stylet forms an entry path, along which one or more dilators can be sequentially advanced, in order to dilate soft tissues between the incision and the target interspinous process space 82. The sleeve 97 can then be advanced through the entry path. Following selection of an implant 10 having a size appropriate for a desired amount of interspinous distraction, the implant 10 can be inserted, held by the insertion device 92, advanced through the sleeve 97, up to the target interspinous process space 82, after which the implant can be inserted into the interspinous process space. In the case of threaded implants, rotational motion is applied to advance the implant 10 and distract the adjacent spinous processes 81a, 81b. In the case of non-threaded implants, laterally-directed pressure can be applied until the implant is in the desired position, after which any engagement elements, if provided, can be deployed.

Figure 12:
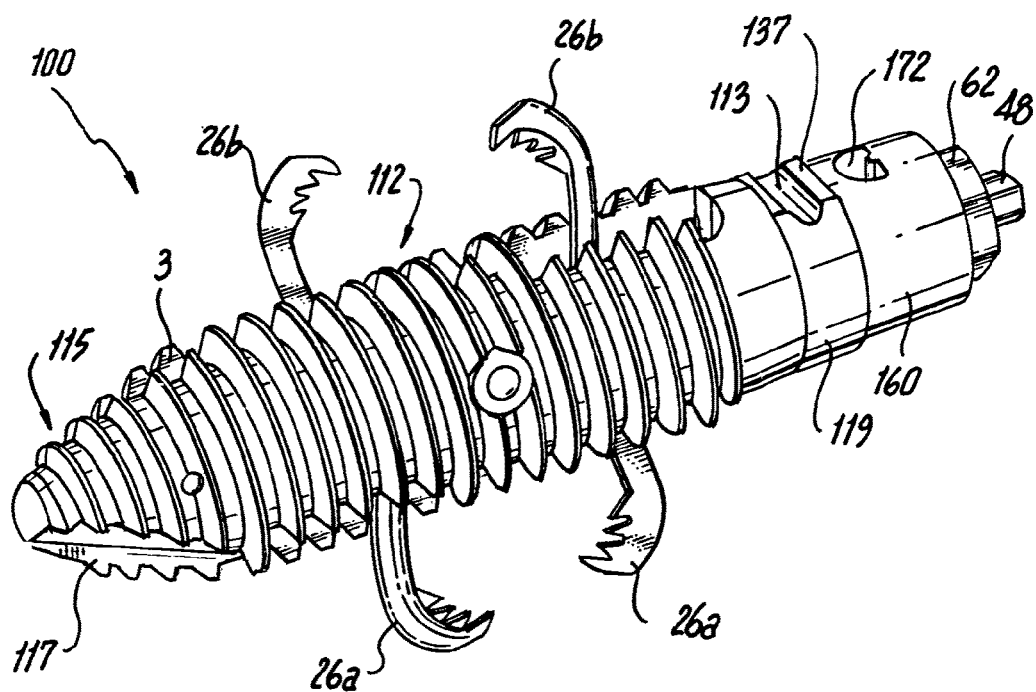
FIG. 12 is a perspective view of a further embodiment of an interspinous implant in accordance with the invention, having an integral tap chamfer on a leading end thereof, providing self-tapping capability, eliminating a need to separately tap an interspinous process space.
Figure 13:
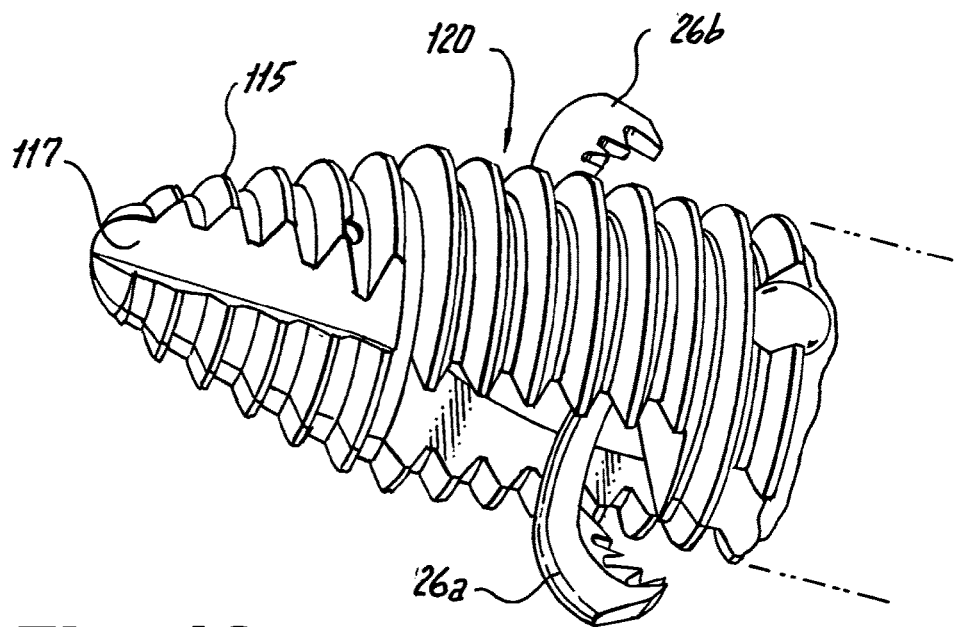
FIG. 13 is a partial lower perspective view of the interspinous implant of FIG. 12.

FIGS. 12 and 13 are perspective views of a further embodiment of an interspinous implant 100 in accordance with the invention, having an integral tap chamfer 117 on a leading end 115 thereof, providing self-tapping capability, and thus eliminating a need to separately tap a target interspinous process space (e.g. 82). Elements identical to those described in connection with above-described embodiments are indicated with the same reference numbers.

The implant 100 is similar in many respects to the implant 10 of FIGS. 1-7, and includes a threaded body 112, claw portions 26a, 26b on respective engagement arms, an optional detent 3, lock nut 62, end fitting 48 for actuation of the engagement arms, as described in connection with the embodiment of FIGS. 1-7. In this embodiment, however, a proximal cap 119 is provided with the body 112, and is preferably unitarily formed, such as by machining and/or casting from a metal material, such as titanium, a surgical grade stainless steel or other suitable biocompatible material, such as PEEK, for example. The proximal cap 119 is configured to receive the proximal end of the body 12, thereby maintaining the portions of the body, split longitudinally, in mutual contact. The proximal cap 119 is preferably press-fit on the body during assembly thereof, but could be attached in another suitable manner, which may include friction fit, mutual threaded engagement or the like. The proximal cap 119 includes an annular toothed surface 70 (see, for example, FIG. 15), which is a unitary embodiment of such a feature, provided in separate halves 70a, 70b in above-described embodiments. The proximal cap 119 is also provided with opposed circumferentially tangential grooves 113, in planar portions 137, also provided on the proximal cap. The planar portions 137 and the grooves 113, respectively prevent unintentional relative rotational and axial movement between the implant 100 and an insertion device. The locking cap 160 includes two circumferentially opposed ports 172, provided therein.

Figure 14:
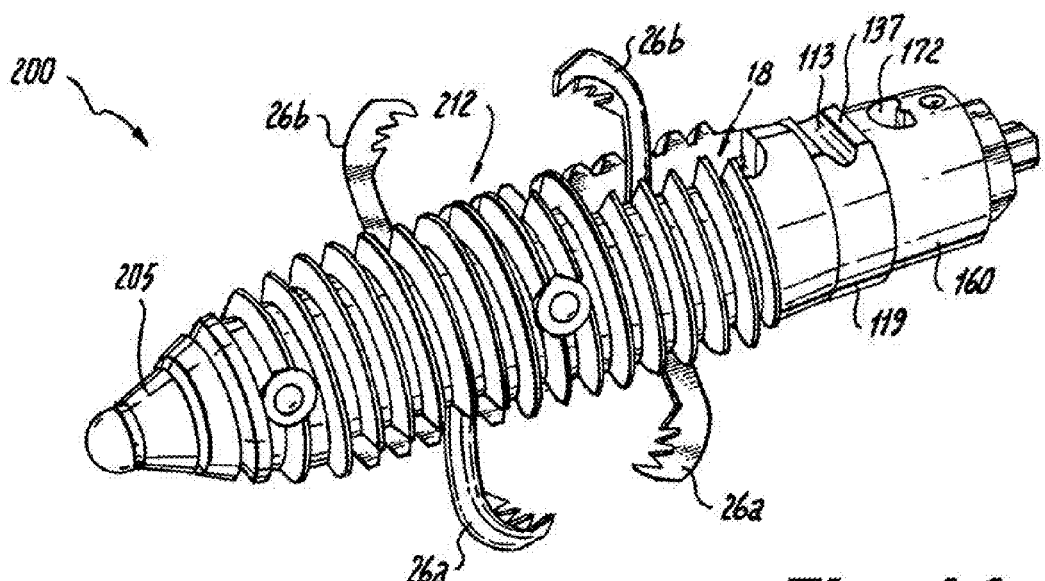
FIG. 14 is a perspective view of a further embodiment of an interspinous implant in accordance with the invention, having a separately formed tip portion and internal core (FIG. 15), for additional structural rigidity.
Figure 15:
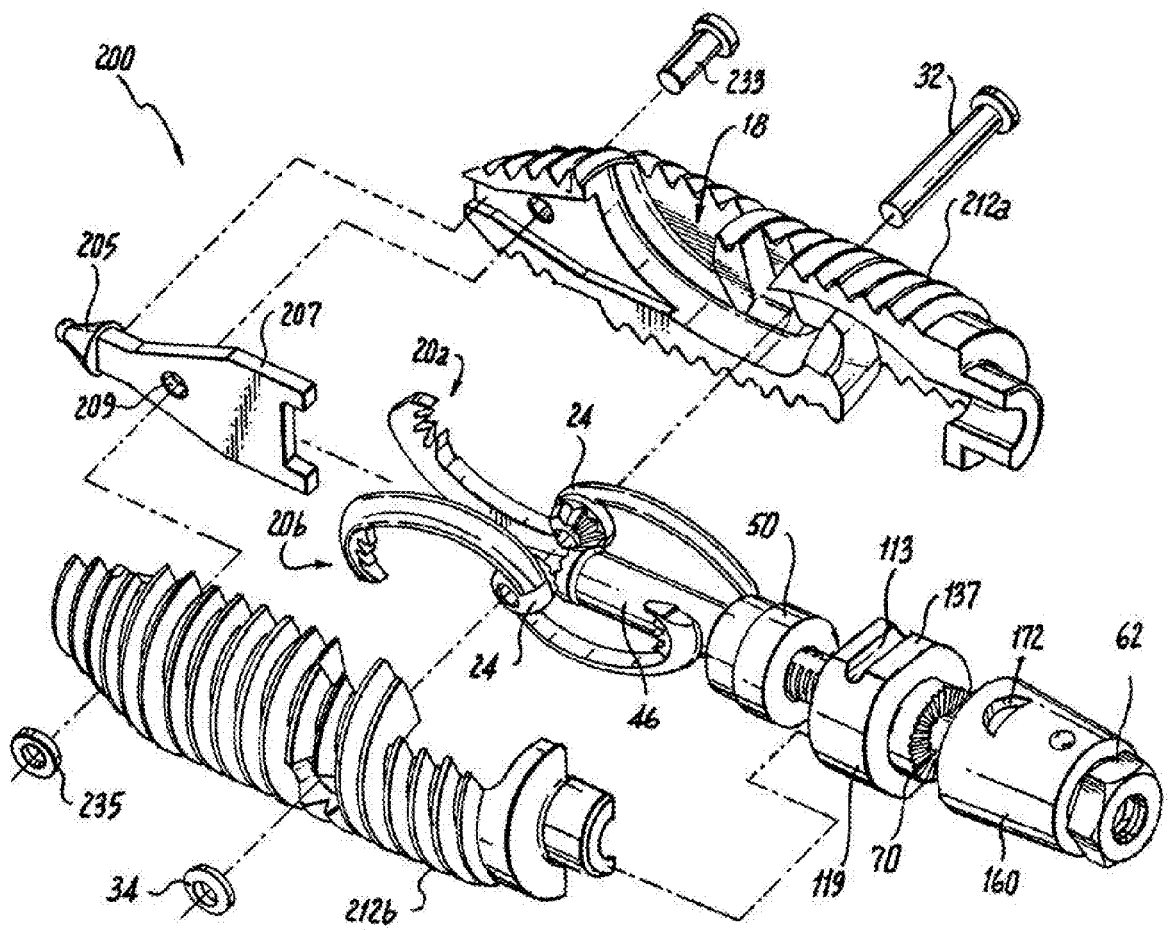
FIG. 15 is an exploded view of the interspinous implant of FIG. 14.

FIGS. 14 and 15 are perspective and exploded perspective views of a further embodiment of an interspinous implant 200 in accordance with the invention, having a separately formed tip portion 205 and internal core 207, which provide additional structural rigidity to the implant 200. Elements identical to those described in connection with above-described embodiments are indicated with the same reference numbers. Many elements are essentially the same as those of the foregoing embodiments, as is the function of the engagement arms and their respective engagement claws 26a, 26b. The proximal cap 119 is configured and functions like that of the embodiment of FIGS. 12 and 13. The exploded view of FIG. 15 illustrates one example configuration of a proximal end portion of the body portions 12a, 12b, where they are engaged by the proximal cap 119.

The implant 200 differs in that the tip portion 205, and integral core 207 are provided, and in conjunction with the proximal cap 119, provide a strong overall structure to the implant 200. The tip 205 and core 207 are preferably formed of a relatively rigid material, such as a titanium alloy, or alternatively of another suitable material. A pin 233 is preferably provided for mutually engaging the distal portion of the body halves 212a, 212b, the core 207 and tip 205, by way of an aperture 209 therethrough. The pin 233 is secured in a suitable manner, such as with a clip 235, by laser welding or other suitable connection.

Figure 16:
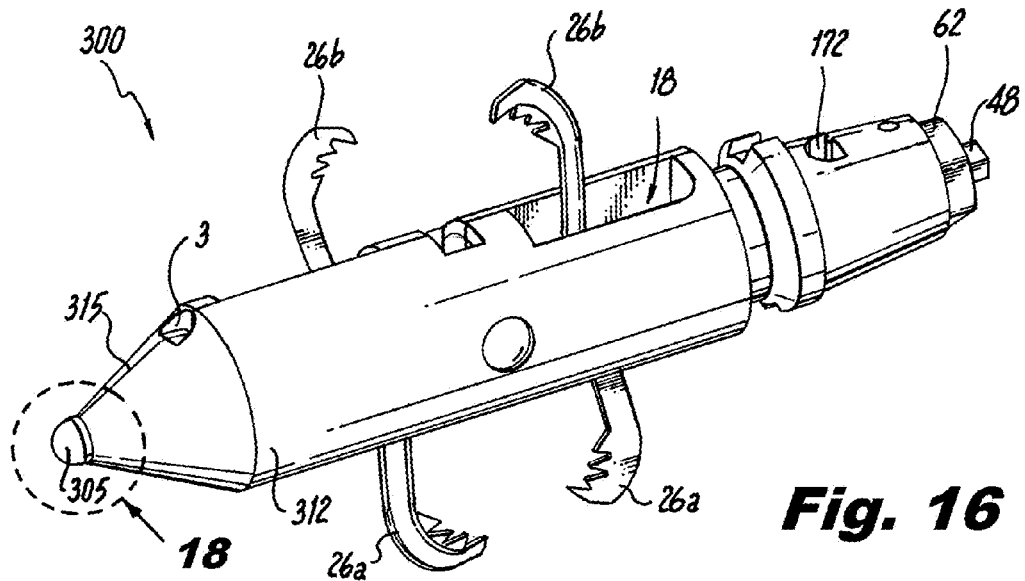
FIG. 16 is a perspective view of a further embodiment of an interspinous implant in accordance with the invention, having an outer surface that is not threaded.
Figure 18:
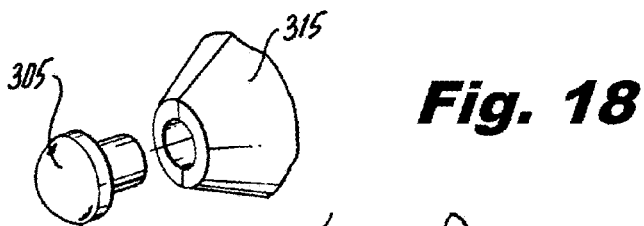
FIG. 18 is a partial exploded view of an alternative arrangement for a distal tip portion for interspinous implants in accordance with the invention.
Figure 17:
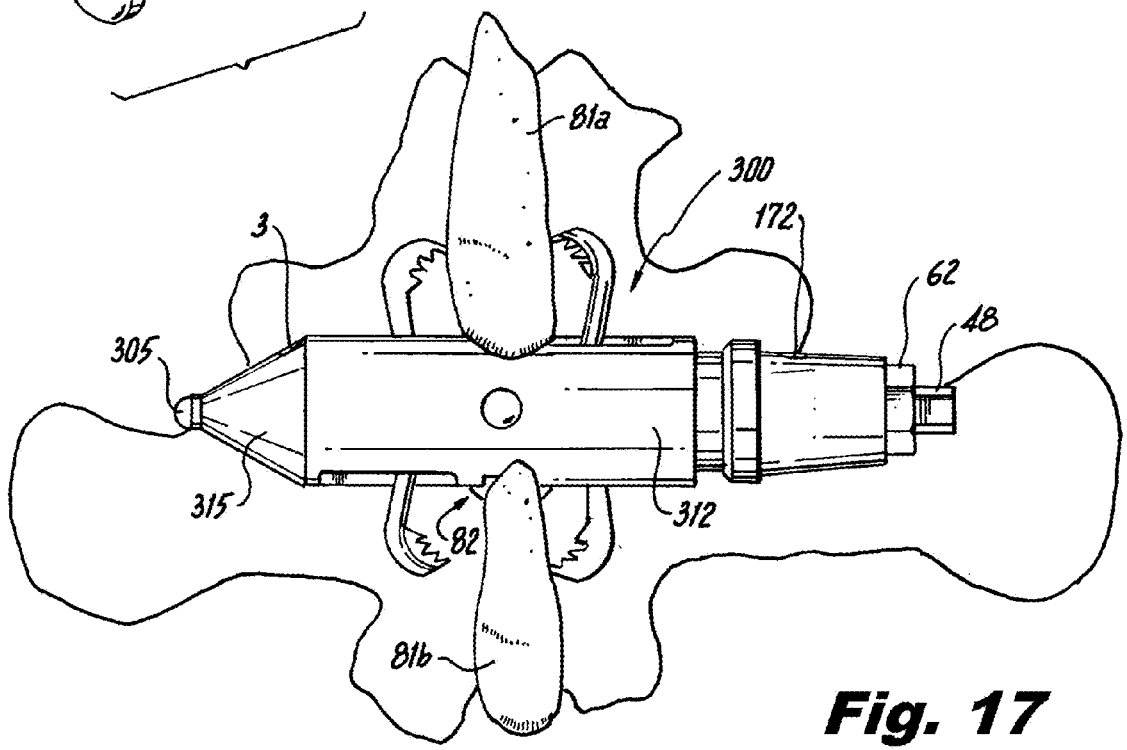
FIG. 17 is a rear (dorsal) view illustrating placement of the interspinous implant of FIG. 16, placed in a target interspinous process space.

FIG. 16 is a perspective view of a further embodiment of an interspinous implant 300 in accordance with the invention, having a body 312 with an outer surface, including leading surface 315 and tip 305, that are not threaded. FIG. 17 is a rear (dorsal) view illustrating placement of the interspinous implant 300, placed in a target interspinous process space 82, and FIG. 18 is a partial exploded view of an alternative arrangement for a distal tip portion for interspinous implants in accordance with the invention. Elements identical to those described in connection with above-described embodiments are indicated with the same reference numbers.

As discussed above, advancement of the implant 300 differs from threaded implants described herein, in that rotational movement does not advance the implant into the target interspinous process space, and lateral force must be applied instead.

The internal structure of the implant 300 can include a core, as with the embodiment of FIGS. 14 and 15, and can be integral with the tip 305, or alternatively, the tip 305 can be separately formed and inserted into the assembly of the implant 300. A proximal recess 3 can optionally be provided to facilitate engagement with an insertion device, as described above.

While the devices and methods of the subject invention have been shown and described with reference to select preferred embodiments, those skilled in the art will readily appreciate that changes and/or modifications may be made thereto without departing from the spirit and scope of the subject invention.

What is claimed is:

1. A spinal implant comprising:
an elongated threaded body portion dimensioned and configured for percutaneous introduction into the interspinous process space and having a longitudinal axis, the body portion including an interior cavity and a pair of deployable engagement members mounted to rotate in tandem about a common axis extending transverse to the longitudinal axis of the body portion between a stowed position retracted within the interior cavity of the body portion and a deployed position extended from the interior cavity of the body portion for engaging the spinous process,
wherein each engagement member includes a pair of curved engagement arms extending radially outwardly from a central hub and each engagement arm includes a distal claw portion having a plurality of teeth for engaging the spinous process.

2. A spinal implant as recited in claim 1, further comprising a drive assembly extending into the interior cavity of the threaded body portion for selectively moving the engagement members in tandem from the stowed position to the deployed position.

3. A spinal implant as recited in claim 2, further comprising means operatively associated with the drive assembly for selectively locking the engagement members in the deployed position.

4. A spinal implant as recited in claim 1, wherein the drive assembly includes a main drive shaft that extends into the interior cavity of the body portion along the longitudinal axis of the body portion.

5. A spinal implant as recited in claim 1, wherein the threaded body portion includes an outer profile, tapering axially inwardly in a distal nose portion thereof, configured to gradually distract adjacent spinous processes during insertion of the implant into the interspinous process space.

6. A spinal implant as recited in claim 5, wherein threads are provided on the body portion, and extend at least partially over the nose portion thereof.

7. A spinal implant as recited in claim 6, wherein the distal nose portion tapers axially inwardly with respect to a central region of the body, by an angle of about 30 degrees, with respect to a longitudinal axis thereof.

8. A spinal implant as recited in claim 1, further comprising an interior core portion adapted and configured for rigidifying the spinal implant.

9. A spinal implant as recited in claim 8, wherein the core portion includes an integral tip portion, arranged at the distal end of the implant.

10. A spinal implant as recited in claim 1, wherein the body portion includes a separately formed proximal portion, formed of a material dissimilar from a material from which a central portion of the body portion is formed.

11. A spinal implant as recited in claim 10, wherein the proximal portion is formed of a metal material, and the central portion of the body portion is formed of a polymeric material.

12. A spinal implant as recited in claim 1, wherein the teeth are dissimilar.

13. A spinal implant comprising:
a) A threaded elongated body portion dimensioned and configured for percutaneous introduction into the interspinous process space, the threaded elongated body portion defining a longitudinal axis and having an interior cavity;
b) a pair of deployable engagement members adapted and configured to move in tandem about a common axis extending transverse to the longitudinal axis of the threaded elongated body portion between a stowed position retracted within the interior cavity of the threaded elongated body portion and a deployed position extended from the interior cavity of the threaded elongated body portion for engaging the spinous process; and
c) a rotatable drive shaft extending into the interior cavity of the threaded elongated body portion along the longitudinal axis thereof for selectively moving the engagement members in tandem from the stowed position to the deployed position,
wherein two engagement members are provided for engaging spinous process, each engagement member includes a pair of curved engagement arms extending radially outwardly from a central hub, and each engagement arm includes a distal claw portion having a plurality of teeth for engaging the spinous process.

14. A spinal implant as recited in claim 13, a locking cap operatively associated with the rotatable drive shaft and the body portion for selectively locking the engagement members in the deployed position.

15. A spinal implant as recited in claim 13, wherein the teeth are dissimilar.

16. A method of lateral insertion of a spinal implant into an interspinous process space, comprising the steps of:
a) forming an incision in a patient's skin, lateral from a target interspinous process space, in which the implant is to be placed;
b) inserting a stylet through the incision, laterally to the target interspinous process space, using an internal imaging technique, to form an entry path;
c) inserting one or more dilators, sequentially, along the entry path to dilate soft tissues between the incision and the target interspinous process space;
d) inserting a sleeve through the entry path;
e) selecting an implant having a size appropriate for a desired amount of interspinous distraction and a pair of deployable engagement members for engaging the spinous process, the engagement members being mounted for rotational deployment in tandem about a common axis that extends transverse to a longitudinal axis of the implant, wherein each engagement member includes a pair of curved engagement arms extending radially outwardly from a central hub, and each engagement arm includes a distal claw portion having a plurality of teeth for engaging the spinous process;
f) inserting the implant, held by an insertion device, through the sleeve, up to the target interspinous process space;
g) advancing the implant into the interspinous process space; and
h) deploying the pair of engagement members.

17. A method of lateral insertion of a spinal implant into an interspinous process space of claim 16, wherein the advancing step includes rotating the implant along a longitudinal axis thereof, to effect axial advancement of the implant by way of threads formed on an outer surface thereof.

18. A method of lateral insertion of a spinal implant into an interspinous process space of claim 16, wherein the teeth are dissimilar.

* * * * *